United States Patent
Faivre et al.

(10) Patent No.: US 9,474,783 B2
(45) Date of Patent: Oct. 25, 2016

(54) HIP/PAP PROTEIN AND DERIVATIVES THEREOF FOR USE IN TREATING CANCER

(71) Applicants: ALFACT INNOVATION, Paris (FR); INSERM (INSTITUT NATIONAL DE LA SANTE ET DE LA RECHERCHE MEDICALE), Paris (FR); UNIVERSITE PARIS SUD, Orsay (FR)

(72) Inventors: Jamila Faivre, Paris (FR); Eric Vibert, Paris (FR); Marion Darnaud, Paris (FR); Laure Jamot, Paris (FR); Christian Brechot, Paris (FR); Paul Amouyal, Sevres (FR); Gilles Amouyal, Paris (FR)

(73) Assignees: ALFACT INNOVATION, Paris (FR); INSERM (INSTITUT NATIONAL DE LA SANTE ET DE LA RECHERCHE MEDICALE), Paris (FR); UNIVERSITE PARIS SUD, Paris (FR)

( * ) Notice: Subject to any disclaimer, the term of this patent is extended or adjusted under 35 U.S.C. 154(b) by 0 days.

(21) Appl. No.: 14/415,320

(22) PCT Filed: Jul. 18, 2013

(86) PCT No.: PCT/EP2013/065233
§ 371 (c)(1),
(2) Date: Jan. 16, 2015

(87) PCT Pub. No.: WO2014/013032
PCT Pub. Date: Jan. 23, 2014

(65) Prior Publication Data
US 2015/0190465 A1  Jul. 9, 2015

(30) Foreign Application Priority Data

Jul. 19, 2012 (EP) .................. 12305877

(51) Int. Cl.
A61K 38/17 (2006.01)
A61K 31/704 (2006.01)

(52) U.S. Cl.
CPC ......... *A61K 38/1732* (2013.01); *A61K 31/704* (2013.01); *A61K 38/17* (2013.01)

(58) Field of Classification Search
None
See application file for complete search history.

(56) References Cited

U.S. PATENT DOCUMENTS

2013/0216545 A1* 8/2013 Levetan ............... C07K 14/474
424/139.1

FOREIGN PATENT DOCUMENTS

WO  2008/031854 A2  3/2008

OTHER PUBLICATIONS

Davies 2005 "FKBP52" IJBCB 37:42-47.*
Kirsch 2000 "BMP-2 antagonists emerge from alterations in the low-affinity binding epitope for receptor BMPR-II" EMBO 19(13):3314-3324.*

* cited by examiner

*Primary Examiner* — Adam M Weidner
(74) *Attorney, Agent, or Firm* — Whitham, Curtis & Cook, P.C.

(57) ABSTRACT

This invention concerns a HIP/PAP protein or derivative thereof, for its use in treating or managing cancer and preferentially solid tumors.

13 Claims, 3 Drawing Sheets

SEQUENCE LISTING

```
<160> NUMBER OF SEQ ID NOS: 4

<210> SEQ ID NO 1
<211> LENGTH: 149
<212> TYPE: PRT
<213> ORGANISM: Homo sapiens

<400> SEQUENCE: 1

Glu Glu Pro Gln Arg Glu Leu Pro Ser Ala Arg Ile Arg Cys Pro Lys
1               5                   10                  15

Gly Ser Lys Ala Tyr Gly Ser His Cys Tyr Ala Leu Phe Leu Ser Pro
            20                  25                  30

Lys Ser Trp Thr Asp Ala Asp Leu Ala Cys Gln Lys Arg Pro Ser Gly
        35                  40                  45

Asn Leu Val Ser Val Leu Ser Gly Ala Glu Gly Ser Phe Val Ser Ser
    50                  55                  60

Leu Val Lys Ser Ile Gly Asn Ser Tyr Ser Tyr Val Trp Ile Gly Leu
65                  70                  75                  80

His Asp Pro Thr Gln Gly Thr Glu Pro Asn Gly Glu Gly Trp Glu Trp
                85                  90                  95

Ser Ser Ser Asp Val Met Asn Tyr Phe Ala Trp Glu Arg Asn Pro Ser
            100                 105                 110
```

```
Thr Ile Ser Ser Pro Gly His Cys Ala Ser Leu Ser Arg Ser Thr Ala
            115                 120                 125

Phe Leu Arg Trp Lys Asp Tyr Asn Cys Asn Val Arg Leu Pro Tyr Val
130                 135                 140

Cys Lys Phe Thr Asp
145

<210> SEQ ID NO 2
<211> LENGTH: 138
<212> TYPE: PRT
<213> ORGANISM: Homo sapiens

<400> SEQUENCE: 2

Ile Arg Cys Pro Lys Gly Ser Lys Ala Tyr Gly Ser His Cys Tyr Ala
1               5                   10                  15

Leu Phe Leu Ser Pro Lys Ser Trp Thr Asp Ala Asp Leu Ala Cys Gln
            20                  25                  30

Lys Arg Pro Ser Gly Asn Leu Val Ser Val Leu Ser Gly Ala Glu Gly
        35                  40                  45

Ser Phe Val Ser Ser Leu Val Lys Ser Ile Gly Asn Ser Tyr Ser Tyr
    50                  55                  60

Val Trp Ile Gly Leu His Asp Pro Thr Gln Gly Thr Glu Pro Asn Gly
65                  70                  75                  80

Glu Gly Trp Glu Trp Ser Ser Ser Asp Val Met Asn Tyr Phe Ala Trp
                85                  90                  95

Glu Arg Asn Pro Ser Thr Ile Ser Ser Pro Gly His Cys Ala Ser Leu
            100                 105                 110

Ser Arg Ser Thr Ala Phe Leu Arg Trp Lys Asp Tyr Asn Cys Asn Val
        115                 120                 125

Arg Leu Pro Tyr Val Cys Lys Phe Thr Asp
    130                 135

<210> SEQ ID NO 3
<211> LENGTH: 150
<212> TYPE: PRT
<213> ORGANISM: Homo sapiens

<400> SEQUENCE: 3

Met Glu Glu Pro Gln Arg Glu Leu Pro Ser Ala Arg Ile Arg Cys Pro
1               5                   10                  15

Lys Gly Ser Lys Ala Tyr Gly Ser His Cys Tyr Ala Leu Phe Leu Ser
            20                  25                  30

Pro Lys Ser Trp Thr Asp Ala Asp Leu Ala Cys Gln Lys Arg Pro Ser
        35                  40                  45

Gly Asn Leu Val Ser Val Leu Ser Gly Ala Glu Gly Ser Phe Val Ser
    50                  55                  60

Ser Leu Val Lys Ser Ile Gly Asn Ser Tyr Ser Tyr Val Trp Ile Gly
65                  70                  75                  80

Leu His Asp Pro Thr Gln Gly Thr Glu Pro Asn Gly Glu Gly Trp Glu
                85                  90                  95

Trp Ser Ser Ser Asp Val Met Asn Tyr Phe Ala Trp Glu Arg Asn Pro
            100                 105                 110

Ser Thr Ile Ser Ser Pro Gly His Cys Ala Ser Leu Ser Arg Ser Thr
        115                 120                 125

Ala Phe Leu Arg Trp Lys Asp Tyr Asn Cys Asn Val Arg Leu Pro Tyr
    130                 135                 140
```

```
Val Cys Lys Phe Thr Asp
145                 150

<210> SEQ ID NO 4
<211> LENGTH: 175
<212> TYPE: PRT
<213> ORGANISM: Homo sapiens

<400> SEQUENCE: 4

Met Leu Pro Pro Met Ala Leu Pro Ser Val Ser Trp Met Leu Leu Ser
1               5                   10                  15

Cys Leu Met Leu Leu Ser Gln Val Gln Gly Glu Glu Pro Gln Arg Glu
            20                  25                  30

Leu Pro Ser Ala Arg Ile Arg Cys Pro Lys Gly Ser Lys Ala Tyr Gly
        35                  40                  45

Ser His Cys Tyr Ala Leu Phe Leu Ser Pro Lys Ser Trp Thr Asp Ala
    50                  55                  60

Asp Leu Ala Cys Gln Lys Arg Pro Ser Gly Asn Leu Val Ser Val Leu
65                  70                  75                  80

Ser Gly Ala Glu Gly Ser Phe Val Ser Ser Leu Val Lys Ser Ile Gly
                85                  90                  95

Asn Ser Tyr Ser Tyr Val Trp Ile Gly Leu His Asp Pro Thr Gln Gly
            100                 105                 110

Thr Glu Pro Asn Gly Glu Gly Trp Glu Trp Ser Ser Ser Asp Val Met
        115                 120                 125

Asn Tyr Phe Ala Trp Glu Arg Asn Pro Ser Thr Ile Ser Ser Pro Gly
    130                 135                 140

His Cys Ala Ser Leu Ser Arg Ser Thr Ala Phe Leu Arg Trp Lys Asp
145                 150                 155                 160

Tyr Asn Cys Asn Val Arg Leu Pro Tyr Val Cys Lys Phe Thr Asp
                165                 170                 175
```

HIP/PAP PROTEIN AND DERIVATIVES THEREOF FOR USE IN TREATING CANCER

FIELD OF THE INVENTION

This invention related to the field of cancer therapeutics and in particular to the HIP/PAP protein or derivative thereof for use in treating, and/or managing cancer. HIP/PAP protein according to the invention may be administered alone or in combination with other therapeutics such as cytotoxic agents and/or any conventional treatment of cancer.

BACKGROUND OF THE INVENTION

Despite the enormous variety of cancers which are described in details in the medical literature, such as cancer of the lung, colon, rectum, prostate, breast, brain, liver and intestine, all type of cancers are characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis).

Malignant transformation of normal cells is a complex process featuring frequent genetic and epigenetic alterations that lead to the activation of oncogenes and inactivation of tumor suppressor genes (Kodama et al., In Vivo. 2000 November-December; 14(6):725-34). Contrary to healthy cells that control their own growth and will goes into apoptosis if they become unhealthy, neoplastic cells escape this protective system and grow uncontrollably.

HIP/PAP has been shown to combine mitogenic and antiapoptotic functions through the PKA signalling pathway. In particular HIP/PAP has been demonstrated to promote liver regeneration and may therefore be particularly useful in case of liver resection in order to improve liver function and suppress or limit liver failure. Indeed, using an in vivo model of liver failure (e.g.: HIP/PAP and c-myc bi-transgenic mice, in which c-myc is specifically expressed in the liver using woodchuck hepatitis regulatory sequences), it has been shown that overexpression of HIP/PAP improved mice survival, (U.S. patent application Ser. No. 13/032,521 and WO 2004/112824, Simon et al, FASEB J. 2003 August; 17(11): 1441-50).

While the expression of HIP/PAP has been shown to be negatively correlated with the depth of invasions of CRC (Colorectal carcinoma), no significant relationship has been found between expression of PAP protein and the clinical outcome of patients, Duke's state of tumors, or tumor localization, size or differentiation degree (Zheng et al., J Histochem Cytochem. 2011 January; 59(1):106-15; Rechreche et al., Int J Cancer. 1999 May 31; 81(5):688-94). Furthermore, HIP/PAP is highly expressed during human primary liver cancer and is a member of the Reg family that has been suggested to function as tissue mitogens (Dieckgraefe et al., U.S. Pat. No. 7,510,708).

The incidence of cancer continues to climb as the general population ages, as new cancers develop, and as susceptible populations (e.g., people infected with AIDS or excessively exposed to sunlight) grow. A tremendous demand therefore exists for new method and compositions that can be used to treat patients with cancer.

Current cancer therapies may involve surgery, chemotherapy, hormonal therapy and/or radiation treatment to eradicate neoplastic cells in a patient (see, for example, Stocldale, 1998, *Medicine*, vol. 3, Rubenstein and Federman, eds., Chapter 12, Section IV). Recently, cancer therapy could also involve biological therapy or immunotherapy. All of the approaches pose significant drawbacks for the patient. Surgery for example, may be contraindicated due to the health of a patient. Additionally, surgery may not completely remove neoplastic tissue. Further, radiation therapy as well as chemotherapy, hormonal therapy and biological therapy elicit numerous and serious side effects.

Therefore, there is still a significant need for alternative safe and effective composition for use in treating and/or managing cancer, while reducing or avoiding the toxicities and/or side effects associated with the conventional treatments.

SUMMARY OF THE INVENTION

Very surprisingly, the authors have now demonstrated that HIP/PAP administration lowered tumor progression and potentiates the effect anti-cancer treatment.

Therefore, the present invention relates to HIP/PAP protein or derivatives thereof for its use in treating and/or managing cancer and preferentially solid tumors.

In particular embodiment of the invention, the HIP/PAP protein derivatives comprise an amino acid sequence having at least 90% amino acid identity with a polypeptide selected from the group consisting of the polypeptide of SEQ ID No 1 to 4.

The present invention also relates to pharmaceutical compositions comprising an effective amount of the HIP/PAP protein or derivative thereof, for use in treating and/or managing cancer and preferentially solid tumors.

According to the invention HIP/PAP protein or its derivatives can be used in treating and/or managing various cancers such as cancers selected from the group consisting of: lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, cancer of the urinary tract, breast cancer, colon cancer, rectal cancer, colorectal cancer, small intestine cancer, endometrial or uterine carcinoma, salivary gland carcinoma, kidney or renal cancer, prostate cancer, vulval cancer, thyroid cancer, hepatic carcinoma, anal carcinoma, penile carcinoma, brain, as well as head and neck cancers.

In particular embodiments of the invention HIP/PAP protein or derivative thereof may be administered in combination with at least a second active agent and/or any conventional method of treating or managing cancer.

Another aspect of the invention relates to a product comprising at least (a) the HIP/PAP protein or derivative thereof and (b) a cytotoxic agent for use as a combined preparation for simultaneous, separate or sequential use in treating or managing cancer.

Another aspect of the invention relates to the use of HIP/PAP protein or derivative thereof for improving the efficiency of another cancer treatment.

In particular embodiments of the invention said other cancer treatments encompasse surgery and/or the administration to the patient of an anti-tumoral active agent.

DETAILED DESCRIPTION

On the opposite of the mitogenic and anti-apoptotic properties suggested by the previous art, the authors have discovered that HIP/PAP administration lowered tumor progression and potentiated the effect of anti-cancer treatments.

In particular they have shown that HIP/PAP administration lowered the progression of secondary hepatic tumor from colorectal metastases both after minor or major partial hepatectomy. Further, HIP/PAP protein or derivative thereof potentiates the effect of a second chemotherapeutic agent, such as doxorubicin when administered in combination. Lastly, HIP/PAP protein or derivative thereof decreases in vitro survival and growth of cancer cells and potentiates the effect of a second chemotherapeutic agent typically inhibiting neoplastic cell growth.

Particular compositions, pharmaceutical kits and uses, according to the invention are described in the sections and subsections which follow.

1—HIP/PAP Protein and Derivative Thereof

The present invention relates to a HIP/PAP protein or derivative thereof for its use in treating and/or managing cancer and preferentially solid tumors in mammals.

According to the invention, HIP/PAP protein or derivative thereof can be use as such, or in a pharmaceutical composition comprising at least an effective amount of HIP/PAP protein and/or a derivative thereof in a physiologically acceptable medium.

As used herein, the term "mammals" refers to any animal classified as a mammal (humans, domestic and farm animals as well as zoo, sport and pets animals, such as dogs, cats, cattle, horses, sheep, pigs, goats, rabbits, etc) and in particular to humans.

HIP/PAP protein or derivative thereof, or composition as mentioned above, can be used for treating and/or managing primary and metastatic cancers, and preferentially solid tumors. Typically, HIP/PAP protein or derivative thereof according to the invention reduces neoplastic cell (tumors cells) growth.

In the following specification, the expression "HIP/PAP protein" will include the HIP/PAP protein and its derivatives, as such or in a composition as mentioned above.

As used herein, the term "cancer" describes a large family of diseases, also medically known as malignant neoplasm or tumor. Cancer is characterised by abnormal cell proliferation within normal body tissue with the result that the survival of the body is threatened. Abnormal cancer cells form malignant tumors, and invade nearby parts of the body. Eventually, the cancer may also spread to more distant parts of the body through the lymphatic system or bloodstream thus forming a secondary or metastatic tumor. Therefore the term "cancer" as used herein encompasses both primary malignant tumor (e.g., cancer) and secondary (or metastatic) tumor or cancer. Preferentially, HIP/PAP protein according to the invention is suitable for the treatment of solid tumors. Therefore, as used herein the term "cancer" preferentially includes: lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, cancer of the urinary tract, breast cancer, colon cancer, rectal cancer, colorectal cancer, small intestine cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, brain, as well as head and neck, cancers.

In one embodiment of the invention, HIP/PAP protein is suitable for the treatment of digestive cancers. Digestive cancers according to the invention include but are not limited to hepatocellular carcinoma, liver (or hepatic) cancer, gastric or stomach cancer including gastrointestinal cancer, pancreatic cancer, colorectal cancer.

In another embodiment of the invention, HIP/PAP protein is suitable for the treatment of breast cancers.

HIP/PAP protein is also suitable for treating mammals, preferentially humans, who have been previously treated for cancer and who are not responsive to standard therapies, as well as those who have not been previously treated.

As used herein, the term "treating cancer" refers to the use of HIP/PAP protein, after the onset of symptoms of the cancer. By treating cancer, or cancer treatment, as used herein, it is intended inducing at least one of the following effects: inhibition of tumor cell growth (including, slowing down and complete growth arrest) and/or of cancer cells survival, inhibition of the spread of the cancer (including, slowing down and complete arrest), decrease of the tumor size or weight (inhibition of neoplastic cells growth), reduction of the number of cancer cells in the body, improvement or relief of the symptoms of the disease caused by the cancer. The treatment is considered therapeutic if there is a decrease in mortality and/or an increase in survival and/or a decrease in morbidity.

Therefore an embodiment of the invention relates to a HIP/PAP protein or derivative thereof for its use in inhibiting tumor or cancer cell growth (including, slowing down and complete growth arrest) and/or of cancer cells survival, and/or inhibiting the spread of the cancer (including, slowing down and complete arrest), and/or decreasing the tumor size or weight (inhibition of neoplastic cells growth), and/or reducing the number of cancer cells in the body and/or improving or relieving the symptoms of the disease caused by the cancer.

As used herein, and unless otherwise indicated, the term "managing cancer" encompasses the prophylaxis of cancer as well as delaying or reducing the occurrence of a cancer and/or the recurrence of the cancer in a patient who had previously suffered from cancer and/or lengthening the time a patient who has suffered from a cancer remains in remission.

A "HIP/PAP protein" according to the invention encompasses a protein comprising the amino acid sequence of SEQ ID No 1. The amino acid sequence of SEQ ID No 1 corresponds to the HIP/PAP protein of SEQ ID No 4, depleted from its 26 amino acids N-terminal signal peptide. Specific embodiments of a HIP/PAP protein encompass proteins comprising an amino acid sequence of SEQ ID No 2. The amino acid sequence of SEQ ID No 2 corresponds to the short form of the HIP/PAP protein, and as compared to SEQ ID No 1 is therefore depleted from its 11 amino acids N-terminal propeptide. Other embodiments of a HIP/PAP protein according to the invention encompass proteins comprising an amino acid sequence of SEQ ID No 3. The amino acid sequence of SEQ ID No 3 corresponds to the amino acid SEQ of SEQ ID No 1 further comprising an additional methionine in the N-terminal position. The HIP/PAP protein of SEQ ID No 3 consists of the HIP/PAP protein that is more specifically illustrated in the examples herein, and that is also termed "rcHIP/PAP" or "ALF5755". As illustrated in the examples herein, the HIP/PAP protein of SEQ ID No 3 may be recombinantly produced in *E. coli*. The N-terminal propeptide portion of 12 amino acids (e.g., the 11 amino acid propeptide plus the additional methionine) may also be cleaved in order to obtain a short form of the HIP/PAP protein. According to the invention, the HIP/PAP protein of SEQ ID No 3 can be used either in its long or short form or as a mixture of both the long and the short forms.

HIP/PAP protein according to the invention includes also biologically active derivatives of the protein. Accordingly, a biologically active derivative of HIP/PAP protein includes a HIP/PAP derived peptide that possesses one or more of the following activities:

reducing tumor progression in rats, such as primary or metastatic hepatic tumor progression after partial hepatectomy (for example of 10, 20, 30, 40, 45, 50, 55, 60, 65, 70, 75, 80, 85 and 90%).
  potentiating the anti-neoplastic effect of a second chemotherapeutic agent such as doxorubicin, as exemplified on primary mammary tumor growth inhibition in mice, or any conventional method for the treatment of cancer such as tumor resection or radiotherapy.
  reducing in vitro survival/growth of cancer cells (neoplastic cells) alone or in association with a second chemotherapeutic agent, such as doxorubicin, as exemplified with the decrease of survival/growth of MCF7 and PANC1 cell lines.

Preferably, any embodiment of a HIP/PAP protein, as well as any embodiment of a derivative thereof, consists of a recombinant protein, e.g. a protein that is recombinantly produced in bacterial or animal cells, including insect cells and mammal cells.

In some embodiments, a HIP/PAP protein or a derivative thereof, including a biologically active portion of HIP/PAP as described above, can be isolated from cell or tissue sources by an appropriate purification scheme using standard protein purification techniques. In other embodiments, a HIP/PAP protein or a derivative thereof, including a biologically active portion of HIP/PAP as described above, may be produced by recombinant DNA techniques that are familiar to one skilled in the art. According to further embodiments, a HIP/PAP protein or a biologically active derivative thereof, including the short form of HIP/PAP as described above, may be synthesized chemically using standard peptide synthesis techniques.

An isolated or purified HIP/PAP protein or biologically active derivative thereof, including the short form of HIP/PAP as described above, is substantially free of cellular material or other contamination proteins from the cell or tissue source from which the said protein is derived, or substantially free from chemical precursors when chemically synthesized.

As used herein, a HIP/PAP protein derivative encompasses a protein having at least 90% amino acid identity with a protein selected from the group consisting of SEQ ID No 1, SEQ ID No 2, SEQ ID No 3 and SEQ ID No 4.

As used herein, a protein having at least 90% amino acid identity with a reference protein possesses at least 91%, 92%, 93%, 94%, 95%, 96%, 97%, 98% or 99% amino acid identity with the said reference protein.

To determine the percent identity of two amino acid sequences for the purposes of the instant invention, the sequences are aligned for optimal comparison purposes. For example, gaps can be introduced in one or both of a first and a second amino acid sequence for optimal alignment and non-homologous sequences can be disregarded for comparison purposes.

For optimal comparison purposes, the percent identity of two amino acid sequences can be obtained as described in the book of D. Voet and J. G. Voet, *Biochimie* ($2^{nd}$ Edition, De Boeck & Larcier, 2005, section 7.4, paragraph B). Alignment can be achieved with CLUSTAL W (version 1.82) with the following parameters: (1) CPU MODE=ClustalW mp; (2) ALIGNMENT=<<full>>; (3) OUTPUT FORMAT=<<aln w/numbers>>; (4) OUTPUT ORDER=<<aligned>>; (5) COLOR ALIGNMENT=<<no>>; (6) KTUP (word size)=<<default>>; (7) WINDOW LENGTH=<<default>>; (8) SCORE TYPE=<<percent>>; (9) TOPDIAG=<<default>>; (10) PAIRGAP=<<default>>; (11) PHYLOGENETIC TREE/TREE TYPE=<<none>>; (12) MATRIX=<<default>>; (13) GAP OPEN=<<default>>; (14) END GAPS=<<default>>; (15) GAP EXTENSION=<<default>>; (16) GAP DISTANCES=<<default>>; (17) TREE TYPE=<<cladogram>>et (18) TREE GRAP DISTANCES=<<hide>>.

Biologically active derivatives of HIP/PAP protein include peptides comprising amino acid sequences sufficiently homologous to the full-length amino acid sequence of HIP/PAP of any one of SEQ ID No 1 to 4, which include the same number of amino acids than the corresponding full-length HIP/PAP, and exhibit at least the same biological activity as HIP/PAP.

Biologically active derivatives of HIP/PAP protein include further peptides comprising amino acid sequences sufficiently homologous to the full-length amino acid sequence of HIP/PAP of any one of SEQ ID No 1 to 4, which include more amino adds than the corresponding full-length HIP/PAP, and exhibit at least the same biological activity as HIP/PAP.

In addition to naturally occurring allelic variants of the biologically active portion of HIP/PAP sequences that exist in mammals, the person skilled in the art will further appreciate that changes can be introduced by mutation into the nucleotide sequence of any one of SEQ ID No 1 to 4, thereby leading to changes in the amino acid sequence of HIP/PAP without altering the biological activity of HIP/PAP.

In addition, substitutions of non-essential amino acid can be made in the sequences corresponding to a HIP/PAP protein. A "non-essential" amino acid residue is an amino acid residue that can be altered from the wild-type sequence of HIP/PAP without altering the biological activity, whereas an "essential" amino acid residue is required for biological activity.

Generally, HIP/PAP protein derivatives encompass substances comprising a HIP/PAP protein or a HIP/PAP biologically active portion thereof.

In certain embodiments of these HIP/PAP protein derivatives, the HIP/PAP protein or the HIP/PAP biologically active portion or portion thereof, may be combined or associated with a non-HIP/PAP portion through non-covalent bonds. Illustrative embodiments encompass liposomes comprising a HIP/PAP protein or a HIP/PAP biologically active portion thereof, wherein the non-HIP/PAP portion thereof consist of the liposome particles themselves. Depending of the kind of liposome to be considered, or, alternatively, depending on the process used for manufacturing said liposomes, the HIP/PAP protein, or the biologically active portion or derivative thereof, may be located at the surface of the liposome (e.g. exposed to the liposome outer environment) or alternatively, encapsulated therein.

In certain other embodiments of these HIP/PAP protein derivatives, the HIP/PAP protein or the HIP/PAP biologically active portion thereof may be combined or associated with the non-HIP/PAP portion through covalent bonds. Illustratively, the HIP/PAP protein, or the biologically active portion thereof, may be covalently bound to a non-HIP/PAP portion selected from a protein or a non-protein compound, like a polyethylene glycol molecule, wherein the final HIP/PAP derivative consists of a pegylated HIP/PAP or of a pegylated biologically active portion thereof.

A HIP/PAP protein derivative according to the invention also encompasses HIP/PAP protein derivative, that when considered in its state prior to its administration to a patient in need thereof, may not be "biologically active", provided that the said HIP/PAP protein derivative will be biologically active once administered to the said patient.

A HIP/PAP protein derivative, when considered in its state prior to its administration to a patient in need thereof may already be already "biologically active".

Biologically active HIP/PAP protein derivatives also encompass HIP/PAP chimeric or fusion proteins. As used herein, a chimeric protein or a fusion protein comprises the polypeptides cited above which are fused to a non-HIP/PAP polypeptide. Within the fusion protein, the HIP/PAP polypeptide and the non-HIP/PAP polypeptide are fused to each other. The non-HIP/PAP polypeptide can be fused to the N-terminus or to the C-terminus of the HIP/PAP polypeptide. For example, in one embodiment, the fusion protein is a GST-HIP/PAP fusion protein in which the HIP/PAP sequence is fused to the C-terminus of the GST sequence. Such fusion proteins can facilitate the purification of recombinant HIP/PAP.

In all cases the fusion proteins of the invention are "biologically active" according to the previous definition of this expression herein, which includes that the said fusion proteins possess the same biological activity as the HIP/PAP of SEQ ID No 4.

In the following of the application, HIP/PAP protein will be used in reference to HIP/PAP protein and its derivatives as described above.

The expressions "effective amount", or "effective dosing regimen", as used in the present application refer to a dosing regimen of HIP/PAP protein comprised in the HIP/PAP composition to treat or manage cancer. An effective amount of HIP/PAP protein, for purposes of treatment, or management of tumor, may be determined empirically and in a routine manner.

As used herein, an "effective amount" of an active ingredient such as HIP/PAP protein, or of any active agent disclosed herein, in reference to inhibition of neoplastic cell growth, is an amount capable of inhibiting, to some extent, the growth of target cells. The term includes an amount capable of invoking a growth inhibitory, cytostatic and/or cytotoxic effect and/or apoptosis of the target cells. Typically, a "growth inhibitory amount" of HIP/PAP protein is an amount capable of inhibiting the growth of a cell, especially tumor, e.g., cancer cell, either in vitro or in vivo, and may be determined empirically in a routine manner.

Starting form the results shown in the examples herein, the effective amount of the HIP/PAP protein may range from about 0.1 µg/kg of body weight to about 100 mg/kg of body weight. Although in certain embodiments the effective amount of the HIP/PAP protein may reach more than 10 mg/kg, the said effective amount of the HIP/PAP protein is preferably of less than 5000 µg/kg; which includes less than 4500 µg/kg, 4000 µg/kg, 3500 µg/kg, 3000 µg/kg, 2500 µg/kg or 2000 µg/kg. Preferentially, an effective amount of the HIP/PAP protein encompasses amounts of at least 1 µg/kg, 2 µg/kg, 3 µg/kg, 4 µg/kg, 5 µg/kg, 6 µg/kg, 7 µg/kg, 8 µg/kg, 9 µg/kg, 10 µg/kg, 15 µg/kg, 20 µg/kg, 25 µg/kg, 30 µg/kg, 40 µg/kg, 50 µg/kg, 60 µg/kg, 70 µg/kg, 80 µg/kg, 90 µg/kg, 100 µg/kg, 150 µg/kg, 200 µg/kg, 250 µg/kg, 300 µg/kg, 350 µg/kg, 400 µg/kg, 450 µg/kg, 500 µg/kg, 600 µg/kg, 700 µg/kg, 800 µg/kg, 900 µg/kg, 1 mg/kg or more of body weight of the patient.

In particular embodiments of the invention, HIP/PAP is administered at a dosing regimen comprised between 1 and 1000 µg/kg, preferentially between 5 and 800 µg/kg. A typical effective dose in mouse experiments is comprised between 25 and 60 µg/kg. Interspecies scaling of dosage can be performed in a manner known in the art, e.g. as disclosed in Mordenti et al., Pharmaceut. Res. 8, p. 1351 (1991).

Classically, in human an effective dose of a HIP/PAP started from 3 mg in patients weighing 70 kg which corresponds approximately to 40 µg per kilo of body weight.

Preferentially, an effective dose in human is comprised between 4 and 30 and more preferentially between 4 and 20 mg for patients weighing 70 kg, thus respectively corresponding to approximately 55 to 430 µg/kg and 55 to 285 µg/kg of body weight.

The effective dose of the HIP/PAP protein to be administered, typically in a HIP/PAP composition, will vary depending on factors such as the type of cancer to be treated or managed, the method of administration, the type of compound being used for treatment (the HIP/PAP protein or the derivative that is chosen), the potential combined therapy involved, the patient's age, weight, general medical condition, medical history, etc., and its determination is well within the skill of a practicing physician. Accordingly, it will be necessary for the therapist to adjust the dosage and modify the route of administration as required to obtain the maximal therapeutic effect. The clinician will administer the HIP/PAP protein until a dosage is reached that achieves the desired effect for treatment of the condition in question.

Usually, a pharmaceutical composition according to the invention comprises from 0.1% by weight to 99.9% by weight of the HIP/PAP protein, based on the total weight of the pharmaceutical composition. Thus, a pharmaceutical composition according to the invention may comprise at least 0.5%, 1%, 2%, 3%, 4%, 5%, 6%, 7%, 8%, 9%, 10%, 20%, 30%, 40%, 50%, 60%, 70%, 80%, 90% by weight or more of the HIP/PAP protein, based on the total weight of the pharmaceutical composition. Also, a pharmaceutical composition according to the invention may comprise up to 10% 20%, 30%, 40%, 50%, 60%, 70%, 80%, 90%, 91%, 92%, 93%, 94%, 95%, 96%, 97%, 98%, 99%, 99.5% by weight or less of one or more physiologically acceptable medium, based on the total weight of the pharmaceutical composition. The HIP/PAP protein can be in its short or long form or a mixture of both as previously described.

Typically compositions according to the invention contain an effective amount of the HIP/PAP protein, for example on the order of about 6 µg/ml to about 10 mg/ml, in a physiologically acceptable medium, to prepare pharmaceutically acceptable compositions suitable for effective administration to the patient. Therefore, therapeutic compositions according to the invention may be prepared for storage by mixing the desired molecule having the appropriate degree of purity with optional pharmaceutically acceptable excipients (Remington's Pharmaceutical Sciences, 16th edition, Osol, A. ed. (1980)), in the form of lyophilized formulations or aqueous solutions.

Compositions according to the invention may also comprise at least one further active agent such as cytotoxic agents as described hereafter. For example a composition according to the invention may comprise both HIP/PAP protein (and/or a derivative thereof) as well as doxorubicin, as active agents.

Preserved pharmaceutical compositions suitable for repeated use may comprise, for example, depending mainly on the indication and type of HIP/PAP protein:

a) the HIP/PAP protein and/or the protein derivative thereof;
b) a buffer capable of maintaining the pH in a range of maximum stability of the polypeptide or other molecule in solution, preferably about 1-9;
c) a detergent/surfactant primarily to stabilize the polypeptide or molecule against agitation-induced aggregation;
d) an isotonifier;
e) a preservative for example selected from the group of phenol, benzyl alcohol and a benzethonium halide, e.g., chloride; and
f) water.

Physiologically acceptable excipients are excipients that are non toxic to recipients at the dosages and concentrations employed. Physiologically acceptable medium are medium that are non toxic to recipients at the dosages and concentrations employed.

If the detergent or surfactant employed is non-ionic, it may, for example, be polysorbates (e.g., Polysorbate®, Tween®) 20,80, etc.), PLURONICS™, polyethylene glycol (PEG) or poloxamers (e.g., Poloxamer® 188). The use of non-ionic surfactants permits the formulation to be exposed to shear surface stresses without causing denaturation of the polypeptide. Furthermore, such surfactant-containing formulations may be employed in aerosol devices such as those used in a pulmonary dosing, and needleless jet injector guns (see, e.g., EP 257,956). An isotonifier may be present to ensure isotonicity of a liquid composition of the HIP/PAP protein and includes polyhydric sugar alcohols, preferably trihydric or higher sugar alcohols, such as glycerin, erythritol, arabitol, xylitol, sorbitol, and mannitol. These sugar alcohols can be used alone or in combination. Alternatively, sodium chloride or other appropriate inorganic salts may be used to render the solutions isotonic.

The buffer may, for example, be an acetate, citrate, succinate, or phosphate buffer and other inorganic buffer, depending on the pH desired. The pH of one type of liquid formulation of this invention is buffered in the range of about 4 to 8, preferably about physiological pH.

The preservatives phenol, benzyl alcohol and benzethonium halides, e.g., chloride, are known antimicrobial agents that may be employed. Typical preservatives are for example: octadecyldimethylbenzyl ammonium chloride; hexamethonium chloride; benzalkonium chloride, phenol, butyl or benzyl alcohol; alkyl parabens such as methyl or propyl paraben; catechol; resorcinol; cyclohexanol; 3-pentanol; and m-cresol.

Additive excipients may also include: antioxidants such as ascorbic acid and methionine, chelating agents such as EDTA; sugars such as sucrose, mannitol, trehalose or sorbitol; salt-forming counter-ions, or electrolytes such as protamine sulfate, disodium hydrogen phosphate, potassium hydrogen phosphate, sodium chloride, zinc salts, colloidal silica, magnesium trisilicate, cellulose-based substances, mixtures of saturated vegetable fatty acids, etc.

Excipients for topical or gel-based forms of the HIP/PAP substances according to the invention include polysaccharides such as sodium carboxymethylcellulose or methylcellulose, polyvinylpyrrolidone, polyacrylates, polyoxyethylene-polyoxypropylene-block polymers, polyethylene glycol, and wood wax alcohols.

Active ingredients (HIP/PAP protein as well as any further active agent) may be in the form of a pharmaceutically acceptable salt. The term pharmaceutically acceptable salt refers to salts prepared from pharmaceutically acceptable, non-toxic acids and bases including inorganic and organic acids and bases. Examples of pharmacologically acceptable salts of molecules that form salts and are useful hereunder include alkali metal salts (e.g., sodium salt, potassium salt), alkaline earth metal salts (e.g., calcium salt, magnesium salt), ammonium salts, organic base salts (e.g., pyridine salt, triethylamine salt), inorganic acid salts (e.g., hydrochloride, sulfate, nitrate), and salts of organic acid (e.g., acetate, oxalate, p-toluenesulfonate).

2. Ways of Administration of HIP/PAP Protein

The present invention also encompasses particular ways of administration of the HIP/PAP protein. In particular, the HIP/PAP protein may be administered in combination with at least a second active agent and/or any conventional method (i.e.: further active agent or treatment), wherein the combination is effective for treating and/or managing cancer.

Indeed, it has been shown by the applicant, that HIP/PAP protein provides additive or synergistic effects when given concurrently with at least another active agent, such as doxorubicin, and/or conventional therapy, such as surgery. In particular, it as been demonstrated that administration of a HIP/PAP protein combined to a cytotoxic agent, such as doxorubicin, is suitable for treating breast cancer and that administration of HIP/PAP protein combined with partial hepatectomy lowered hepatic cancer progression.

As used herein, the term "synergistic" refers to combinations according to the invention which are more effective that the additive effects of any two or more single agents.

Typically active agents are cytotoxic agents that include, but are not limited to antimetabolites, antitumor antibiotics, nonsteroidal aromatase inhibitors, immunotherapeutic agents, coordination metal complexes, mitotic inhibitors, topoisomerase inhibitors, hormone therapy agents, alkylating agents, alkaloids or any other antitumor agents such as calcium levofolinate, tyrosine kinase inhibitors, monoclonal antibodies, matrix metalloprotease inhibitors, and farnesyl transferase inhibitors.

Examples of such active agents are: semaxanib; cyclosporin; etanercept; doxycycline; bortezomib; acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

In one embodiment of the invention, the second or more chemotherapeutic agents is preferentially: In fluorouracil, gemcitabine hydrochloride, methotrexate, cytarabine, fludarabine, bleomycin hydrochloride, doxorubicin hydrochloride, daunorubicin hydrochloride, idarubicin hydrochloride, busulfan, carboplatin, cisplatin, cyclophosphamide, dacarbazine, melphalan, anastrozole exemestane trastuzumab, rituximab, toxoids, eg paclitaxel and docetaxel hydrate, vincristine sulfate, vinblastine sulphate, irinotecan hydrochloride, tamoxifen citrate, leuprorelin acetate, calcium levofolinate, tyrosine kinase inhibitors (e.g., gefitinib), monoclonal antibodies (e.g., cetuximab and bevacizumab, trastuzumad), matrix metalloprotease inhibitors, and farnesyltransferase inhibitors. adriamycin, epirubicin, cytosine arabinoside ("Ara-C"), cyclophosphamide, thiotepa, busulfan, cytoxin, toxotere, methotrexate, cisplatin, melphalan, etoposide, ifosfamide, mitoxantrone, vinorelbine, carboplatin, teniposide, daunomycin, carminomycin, aminopterin, dactinomycins, mitomycins, esperamicins (see, U.S. Pat. No. 4,675,187), melphalan and other related nitrogen mustards. Also included in this definition are hormonal agents that act to regulate or inhibit hormone action on tumors such as tamoxifen and onapristone.

In particular embodiments of the present invention, a further active agent is preferentially a growth inhibitory agent and preferentially: agents that block cell cycle progression such as antitumor antibiotics and/or topoisomerase II inhibitors such as as bleomycin hydrochloride, mitomycin C, doxorubicin hydrochloride, daunorubicin hydrochloride, and idarubicin hydrochloride, the vincas (vincristine and vinblastine), DNA alkylating agents such as cisplatin, carboplatin, oxaliplatin, dacarbazine, mechlorethamine, antimetabolite inhibitors of DNA synthesis, such as methotrexate.

In preferred embodiments of the present invention second active agents that can be used in combination with a HIP/PAP protein include but are not limited to 5-fluorouracile, raltitrexed, epirubicin, hepatinib, methotrexate, doxorubicine, daunorubicin, monoclonal antibodies such as cetuximab and trastuzamab, avastin, oxaliplatin, cisplatin, gemcitabine, docetaxel, lapatinib, oxaliplatin and their derivatives.

Said active agents are typically presented in the form of a formulation in admixture with pharmaceutically acceptable carrier, as known in the state of the art. Such a formulation may comprise at least, 1, 2, 3, or 4 active agents for treating and/or managing cancer. Preferentially, at least on e active agent is a cytotoxic agent.

Conventional methods for treating or managing cancer according to the invention include, but are not limited to, surgery, blood transfusion, immunotherapy, biological therapy, radiation therapy and any other non-drug based therapies. In preferred embodiments of the invention, such conventional methods are surgery and radiation therapy. By surgery it is intended partial or complete resection or destruction of tumor tissues using classical surgery or in certain types of tumors such as lung, kidney, breast, bone and liver tumors, radio frequency ablation (RFA) or cryosurgery.

Active agents and/or other conventional methods that may be used in combination with HIP/PAP protein highly depend on the tumor type and can be easily determined by the one skilled in the art.

Additive or synergistic effects of combined uses according to the invention may allow the use of reduced or subactive amount or dosing regimen of the cytotoxic agent(s) (as previously described) and/or the conventional method(s), such as radiation therapy) that is/are combined with the HIP/PAP protein. Such reduced or subactive amount or dosing regimen may prevent or reduce undesirable side effects associated with usual doses (e.g.: doses that would not be used if not combined with HIP/PAP protein) of said cytotoxic agent(s) or conventional method(s).

In cases where a massive resection would be required, but would lead to a high lethal risk for the patient, combined (before, during or after surgery) administration of the HIP/PAP protein, may allow reducing the depth of the resection. Therefore such combined use is particularly adapted for the treatment of liver tumor, when the tumor resection would lead to a lethal "small for size syndrome". At the contrary, it has been previously shown that HIP/PAP protein stimulates liver regeneration. Therefore the combined use of HIP/PAP protein may allow enlarging the use of liver resection while avoiding "small for size syndrome".

When administered in combination with at least a second active agent and/or any conventional method, the administration of HIP/PAP protein, and of a further active agent and/or the use of any conventional methods of treating or managing cancer, is achieved either simultaneously (optionally repeatedly) or sequentially (optionally repeatedly), assuming that the combination is sufficiently closely spaced in time, to enable a beneficial effect for the patient, that is greater or synergistic, over the course of the treatment or the management of the cancer or malignant tumor, than if either a HIP/PAP protein, or the other active agent or conventional method of treatment of the said combination, were administered alone, over the same course of the treatment.

Some embodiments of the invention therefore relates to a HIP/PAP protein, wherein said HIP/PAP protein is characterized in that it is administered in combination with at least a second active agent and/or any conventional method of treating or managing cancer. In a preferred way of administration of HIP/PAP protein, the HIP/PAP protein is administered simultaneously or sequentially to the administration of a further active agent and preferentially a cytotoxic agent as previously described administration of a HIP/PAP protein, may be achieved before, simultaneous with, or after a partial, or complete, surgical resection of the tumor. Said embodiments may also include further administration of at least one cytotoxic agent. Consequently an embodiment of the invention relates to a HIP/PAP protein for use in treating and/or managing cancer wherein said HIP/PAP protein is administered before, during or after a partial or a total resection of the tumor. In a preferred embodiment of the invention the tumor is a liver (hepatic) tumor.

Determination of whether a combination provides a greater beneficial effect in respect of, and over the course of the treatment (curative or prophylactic) of the malignant tumor or cancer will depend upon the condition to be treated or managed but may be achieved routinely by the skilled person. Such combined uses in treating and/or managing cancer allow to stop, lower, or reduce tumor progression and/or to prevent further tumor recurrence or metastasis. When combined with the administration of at least a second active agent (typically a cytotoxic agent and doxorubicin for example), administration of the HIP/PAP protein can be continuous or intermittent (e.g. bolus administration) simultaneously with, before, after or sequentially with, the administration of the further active agent. For example the HIP/PAP protein administration may be achieved continuously for a period of time comprised between a few hours to several days. Such a treatment sequence may be repeated 1 to three times with a period of rest comprised between 24 hours and 1 to 2 months.

HIP/PAP protein may also be administered daily (once or twice per day) during the whole time period of treatment with the second active agent.

A HIP/PAP protein may also be administered, for example, immediately after surgery (i.e.: partial or total resection of the tumor), either continuously (typically intravenously) or by bolus (preferentially intravenously). Bolus injection may be repeated from 2 to 20 times, preferentially from 2 to 10 times with a rest period comprised between 5 hours and 24 hours. Such a treatment sequence may also be repeated 1 to 3 times with a rest period comprised between one to six weeks. An effective dose (for example 20 mg for a human weighing 70 kg) may be administered once daily, or the daily dose may be divided and administered at 12 hourly intervals, for 2 to 6 days starting from the day of the surgery. Preferentially such a dose is administered for 3 days.

The administration of cytotoxic agents (typically chimiotherapy) as well as conventional methods of cancer treatment (typically radiation therapy, hormonal therapy, biological therapy and immunotherapy) is often achieved cyclically (e.g.: administration for a period of time, followed by a rest for a period of time and repeating this sequential administration). Cycling therapies can reduce the development of resistance to one or more of the therapies avoid or reduce the side effects of one of the therapies and/or improve the efficacy of the treatment. The combined administration of the HIP/PAP protein can be achieved simultaneously, with the same or different frequency, before or after said cycling therapies.

The route of administration of HIP/PAP protein is in accordance with known methods, e.g. administration by injection or infusion by intravenous, intramuscular, intracerebral, intraperitoneal, intracerobrospinal, subcutaneous, intraocular, intraarticular, intrasynovial, intrathecal, oral, topical, or inhalation routes, or administration by sustained-release systems as noted below. The HIP/PAP protein is also suitably administered by intralesional or perilesional routes, to exert local as well as systemic therapeutic effects.

When combined with at least a second active agent, administration thereof the HIP/PAP protein can be achieved by the same or different routes of administration. The suitability of a particular route of administration employed for a particular active agent will depend of the active agent itself. Preferred routes of administration for the second active agent as well as for the HIP/PAP protein are known to those of ordinary skill in the art. See, e.g., *Physician's Desk Reference*, 175-1760 (56$^{th}$ ed., 2002). Preferentially the HIP/PAP composition is administered intravenously, subcutaneously or orally. A combined administration of a further active agent may be achieved intravenously or orally for example.

When the HIP/PAP protein is used in combination with any further active agent and/or conventional method, an effective amount of HIP/PAP may be an amount allowing invoking synergistic effects as described in the present application and in particular to invoke a synergistic effect in reference to inhibition of neoplastic cell growth.

In some embodiments, the HIP/PAP protein is administered as a single dose. In some other embodiments, the HIP/PAP protein is administered as a plurality of doses at determined intervals.

The HIP/PAP protein to be used for in vivo administration must be sterile. This is, for example, readily accomplished by filtration through sterile filtration membranes, prior to, or following, lyophilization and reconstitution. The HIP/PAP protein or the protein derivative thereof will ordinarily be stored in lyophilized form or in solution if administered systemically.

If in lyophilized form, the HIP/PAP protein is typically formulated in combination with other ingredients for reconstitution with an appropriate diluent at the moment of use. An example of a liquid formulation of the HIP/PAP protein is a sterile, clear, colorless unpreserved solution filled in a single-dose vial for injection.

Compositions of the therapeutic HIP/PAP protein are generally placed into a container having a sterile access port, for example, an intravenous solution bag or vial having a stopper pierceable by a hypodermic injection needle. The formulations are preferably administered as repeated intravenous (i.v.), subcutaneous (s.c.), or intramuscular (i.m.) injections, or as aerosol formulations suitable for intranasal or intrapulmonary delivery (for intrapulmonary delivery see, e.g., EP 257,956). Conventional depot forms such as, microcapsules, nano-capsules, liposomes, plasters, inhalation forms, nose sprays, sublingual tablets, and sustained-release preparations are for example used. The HIP/PAP protein will typically be formulated in such vehicles at a concentration of about 0.1 mg/ml to 100 mg/ml.

When, the HIP/PAP protein is administered in the form of sustained-released preparations, suitable examples include: semi-permeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al., J. Biomed. Mater. Res., 15: 167-277 (1981) and Langer, Chem. Tech., 12: 98-105 (1982) or poly(vinylalcohol)), polylactides (U.S. Pat. No. 3,773,919, EP 58,481), copolymers of L-glutamic acid and gamma ethyl-L-glutamate (Sidman et al., Biopolymers, 22: 547-556 (1983)), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release HIP/PAP protein preparations also include liposomally entrapped polypeptides. Liposomes containing the polypeptide of interest are prepared by methods known per se: DE 3,218,121; Epstein et al., Proc. Natl. Acad. Sci. USA, 82: 3688-3692 (1985); Hwang et al., Proc. Natl. Acad. Sci. USA, 77: 4030-4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200-800 Angstroms) unilamellar type in which the lipid content is greater than about 30 mol. % cholesterol, the selected proportion being adjusted for the optimal therapy.

3—Combination Products and Pharmaceutical Kits

According to the invention there is also provided a product comprising at least:
- a HIP/PAP protein, for example in the form of a composition as described above in section 1.
- a second active agent in an adapted formulation. Preferentially, said second active agent is a cytotoxic agent, for use as a combined preparation for simultaneous, separate or sequential use in treating or managing cancer.

In particular embodiment of the invention a combination product may comprise at least 2, 3, 4 or 5 active agents.

In particular said combination product is suitable for the treatment of solid tumors such as previously described.

In one embodiment of the invention such combination product is suitable for use in treating and/or managing digestive cancers such as liver cancer, gastro intestinal cancer and pancreatic cancer.

In another embodiment of this invention, said combination products are suitable for use in treating and/or managing breast cancer.

Potential second active agents according to the invention have been previously described in section 3. Preferentially said second active agents are cytotoxic agents. Combined cytotoxic agents depend on the type of cancer to be treated. The applicant has notably shown that such combination product can synergistically reduce or lower tumor size growth, and/or inhibit cancer cell growth/survival.

For use in treating breast cancer, preferred combined agents include but are not limited to, doxoruribicin, trastuzamab, lapatanib, bevacizumab.

For use in treating digestive cancers, preferred combined agents include but are not limited to, 5 fluorouracile, oxaliplatine, raltotrexed, cetuximab, cisplatin, epirubicin, gemcitabin.

In the product according to the invention the HIP/PAP protein and at least a second active agent, are typically presented as separate formulations or compositions, wherein at least one of those formulations comprises a HIP/PAP protein (as a first active agent, typically in the form of a HIP/PAP composition as described above) and at least another one comprises at least a second active agent, preferentially a cytotoxic agent. The HIP/PAP protein and the second active agent at least are each provided in a form suitable for administration in conjunction. The product according to the invention can also be presented as a single formulation including at least a HIP/PAP protein and at least a second active agent (combined preparation).

The invention also encompasses a kit including at least:
(a) a pharmaceutical formulation including a HIP/PAP protein.
(b) a pharmaceutical formulation including a at least a second active agent which component (a) and (b) are each provided in a form suitable for administration sequentially, separately, and/or simultaneously over the course of treatment.

Typically, a kit according to the invention comprises:
(a) a HIP/PAP protein composition as described above in section 1 or 2.
(b) a pharmaceutical formulation including a at least a second active agent and preferentially a cytotoxic agent, which component (a) and (b) are each provided in a form suitable for administration in conjunction with the other for the treatment of cancer as previously described.

A used herein, the term "used in conjunction" includes that the HIP/PAP protein and the at least second active agent are administered (optionally repeatedly) either simultaneously, or sequentially sufficiently closely in time to enable a beneficial effect to the patient (human or animal) that is greater or synergistic over the course of the treatment of cancer than if either a formulation (a) or a formulation (b) are administered (optionally repeatedly) alone in the absence of the other component, over the same course of treatment. Determination of whether a combination provide a greater or a synergistic beneficial effect in respect of and over the course of the cancer treatment will depend upon the type of cancer to be treated or prevented and/or managed and may be routinely achieved by the skilled person.

Typically, a kit according to the invention comprises:
(a) a HIP/PAP protein
(b) doxorubicin
which component (a) and (b) are each provided in a form suitable for administration in conjunction with the other for the treatment of cancer as previously described.

In a combined product or a pharmaceutical kit according to the invention the HIP/PAP composition and the others formulations (at least one or 2, 3, 4 formulations) of the said combined product or the kit may be administered trough different ways of administration such as previously mentioned.

In another embodiment of the present invention, a kit may also comprise at least:
- a pharmaceutical formulation including a HIP/PAP protein, typically in the form of a composition as described above in section 1, and
- instructions, comprising procedure for administering at least one formulation of the kit to a subject in need thereof.

4—Use and Methods According to the Invention

The invention also encompasses the use of HIP/PAP protein or of a composition as described above, for the manufacture of a pharmaceutical composition for the treatment of cancer.

The present invention also deals with the use of a HIP/PAP protein as previously described for the treatment and/or the management of cancer. Particular embodiments of the invention also relate to the use of a HIP/PAP protein, as previously described, for inhibiting tumor cell growth (including, slowing down and complete growth arrest), and/or inhibiting cancer cells survival, and/or inhibiting the spread of the cancer (including, slowing down and complete arrest) and/or decreasing the tumor size or weight (inhibition of neoplastic cells growth) and/or reducing of the number of cancer cells in the body.

Another embodiment of the present invention relates to the use of HIP/PAP for improving the efficiency of another cancer treatment, said other cancer treatment being different from administering HIP/PAP. Said other cancer treatment encompasses conventional methods for treating cancer, such as surgery, blood transfusion, immunotherapy, biological therapy, radiation therapy and any other non-drug based therapies. In a particular embodiment such other treatment encompasses surgery. By surgery it is intended partial or complete resection or destruction of tumor tissues using classical surgery or in certain types of tumors such as lung, kidney, breast, bone and liver tumors, radio frequency ablation (RFA) or cryosurgery. Such other cancer treatment may also comprise administering to a patient an anti-tumoral active agent, in particular a cytotoxic agent such as those previously described in the present application.

Lastly the invention relates to a method for treating or managing cancer comprising the administration of a HIP/PAP protein as previously described.

The invention is non-limitatively illustrated by the examples hereafter. In these examples it will be referred to the following figures:

FIG. 1A: histogram showing the effect on tumor area of a single ALF-5755 100 µg injection after 70% partial hepatectomy, as compared to control vehicle injection. FIG. 1B: histogram showing the effect on tumor area of a single ALF-5755 100 µg injection after 30% partial hepatectomy, as compared to control vehicle injection.

FIG. 3A: effect of doxorubicin at the concentration of 2.5 µM at 24, 48 and 72 hours post-plating on PANC1 cancerous cell growth (dark line: standard culture condition, dashed line: standard culture condition+doxorubicin). FIG. 3B: effect of ALF-5755 in combination to doxorubicin at 24, 48, 72 hours post-plating (dash line: standard culture condition+doxorubicin; dark line: doxorubicin+ALF-5755).

FIG. 4A: effect of doxorubicin at the concentration of 75 µM at 24, 48 and 72 hours post-plating, on the density of mammary cancer cells (dark line: standard culture condition, dashed line: standard culture condition+doxorubicin). FIG. 4B: effect of ALF-5755 in combination to doxorubicin at 24, 48, 72 hours post-plating (dash line: standard culture condition+doxorubicin; dark line: doxorubicin+ALF-5755).

EXAMPLES

1 Material and Methods

A recombinant human HIP/PAP protein was produced in an *E-coli* bacterial system and then has been purified. The resulting product was called ALF-5755. Compared with HIP/PAP protein of SEQ ID no 2, ALF-5755 of SEQ ID No3 has one single extra amino acid, a methionin in the NH2 terminal end.

I) In Vivo Model of Liver Metastases of Colorectal Cancer a) Choice of Animal Model and Tumor Cell Line DHDK12 cell line was derived from liver metastatic cells developed by BDIX rats after 1,2-Dimethylhydrazine) intoxication (chemically-induced cancer). Therefore, all experiments were performed in BDIX rat, the syngenic corresponding strain.

b) Production of DHDK12 Cells

Cells were expanded in vitro in a medium composed of 50% DMEM and 50% F12 (Invitrogen Gibco, Pailsey, GB) complemented with foetal calf serum (10%) and a combination of antibiotics (1% penicillin/streptomycin). Absence of mycoplasm contamination was controlled.

c) Induction of Liver Tumor

At day 1 of the experiment, rats were anesthetized with isofluran gas. After laparotomy they received 20 millions of DHDK12 cells. Cells were injected as a solution in PBS (1 mL total pre-warmed at 37° C.) in the portal vein to ensure a direct diffusion to the liver. Seven days after the procedure, the tumor volume represented up to 30% of the liver.

d) Hepatectomy

At day seven after the injection of cancerous cells, when the tumor was already implanted, two types of hepatectomies were performed: either 30% or 70% of the liver was resected.

e) Treatment

ALF-5755 was injected directly after hepatectomy, in the inferior cave vein, as a solution in PBS (0.3 ml) to achieve a final dose of 0.5 mg/kg. The control group was composed of animals receiving either the equivalent volume of vehicle or no injection.

f) Evaluation of Tumor Expansion

Fourteen days after hepatectomy and treatment, animals were sacrificed. Serial sections of complete liver were performed for each animal (millimetric sections, the number of sections depending on the liver size and morphology). The tumor expansion was assessed by quantifying in square pixels (pixel$^2$) the area of each cancer cells nodule. The complete area of each section was also recorded and a ratio of the nodule/total area was calculated. Analyses were performed with Adobe Photoshop CS3 software.

g) Data Processing and Statistical Analyses

Depending on the experiment, one-tailed t-test or two-tailed Mann-Whitney tests were performed to quantify the effect of ALF-5755 on nodule expansion. Area of nodules was expressed as a percentage of total liver area.

II) In Vivo Model of Primary Mammary Cancer a) Choice of Animal Model and Tumor Cell Line PyMT (Polyoma middle T) cell line was derived from a primary mammary carcinoma induced by PyMT oncogene activation in FBV mice. Therefore, all experiments were performed in FBV mice, the syngenic corresponding strain.

b) Production of PyMT Cells

PyMT mice were sacrificed at 12/13 weeks when presenting a large tumoral mass. The tumour was dissected and cells were dissociated mechanically in DMEM/Glutamax medium and then filtrated. Dead cells were eliminated by centrifugation then viable cells were frozen in aliquots. For tumour implantation in FBV mice, appropriate number of aliquots cells was thawn.

c) Induction of Liver Tumor

At day 1 of the experiment, female mice received 1 million of PyMT cells, within the 8th mammal in the adipose tissue. Cells were injected as a solution in PBS (0.05 ml total pre-warmed at 37° C.).

d) Treatment with ALF-5755

Alzet pumps were implanted in the back of the mice, at the time of PyMT cell injection (experiment 1) or after tumor implantation, when doxorubicin treatment started (experiment 2). The pumps continuously delivered either 43.2 µg of ALF-5755 or vehicle per day for a period of 28 days.

e) Doxorubicin Treatment

Animals started to receive doxorubicin at the time when tumor was detected (15 days after PyMT cells injection for both, ALF-5755 and Vehicle groups) by intra-tumor injection. Animals receive during four weeks, a weekly dose of 1 mg/kg that was known to induce tumor cell-death.

f) Evaluation of Tumor Expansion

At the end of doxorubicin treatment (6 weeks after the beginning of the procedure), animals were sacrificed. The mammary tumors were resected and weighted to evaluate the effect of ALF-5755 treatment. In experiment 2 the survival of animals in ALF-5755 versus Placebo treated animals (in the presence or not of doxorubicin) was also analyzed.

g) Statistical Analyses

The weight of the tumors was compared between the two groups by mean of non-parametric one tailed Mann whitney test. Survival was compared by mean of one-tailed exact Fischer test.

III) In Vitro Model of Mammary and Pancreatic Cell Line Growth a) Cell Culture

The MCF7 (Human breast adenocarcinoma) and PANC1 (Human pancreatic carcinoma, epithelial-like cell line) cell lines were obtained from LGC-Promochem ATCC.

Sub-confluent cultures (70-80%) were split using Trypsin/EDTA and collected in serum free culture medium. Cell concentration was determined using Trypan blue staining and a Mallasez counting chamber.

Briefly, 1,000 cells per well were seeded in 96 well-plates. Cells were maintained in DMEM medium complemented with 1% antibiotics (P/S), and cultured in a humidified atmosphere at 37° C. and 5% CO2.

Cells were maintained in culture for 1 to 3 days (1 plate for each day of analysis). For control of cell survival/growth and validation of the experiments, equivalent cultures were performed in the presence of Foetal calf serum (5%).

b) Treatments and Read-Out

The treatments with ALF-5755, alone or in combination to doxorubicin ($EC_{50}$: 75 µM for MCF7 cells at 24H and 2.5 µM for PANC1 cells at 72H), were performed after cell adhesion (3-4 hours post plating). The effect of increasing concentrations of ALF-5755 ranging from 0 to 2000 ng/ml was investigated over time up to 72 hours. Results for the optimal concentration (2000 ng/mL) only are presented below.

For each time point (24, 48, and 72 hours), 60 minutes prior to cell proliferation measurement, each plate received 10 µL of cell proliferation reagent per well.

The absorbance of the samples was measured against a background control using a 96-well plate reader at 450 nm with a reference wavelength of 690 nm.

c) Data Processing and Statistical Analysis

Raw data are expressed as optical density.

Two-way ANOVA were performed to study ALF-5755 concentration incidence on cell growth and cell growth over time for each condition of culture (+/−ALF-5755 and +/−doxorubicin). Post-hoc Bonferroni were applied to reveal effects of ALF-5755 concentration at each time point, if any.

All indexes of fidelity were calculated for an interval of confidence of 95%.

Results

Example 1

In Vivo Effect of a HIP/PAP Protein on Liver Metastases of Colorectal Cancer

Figure 1:
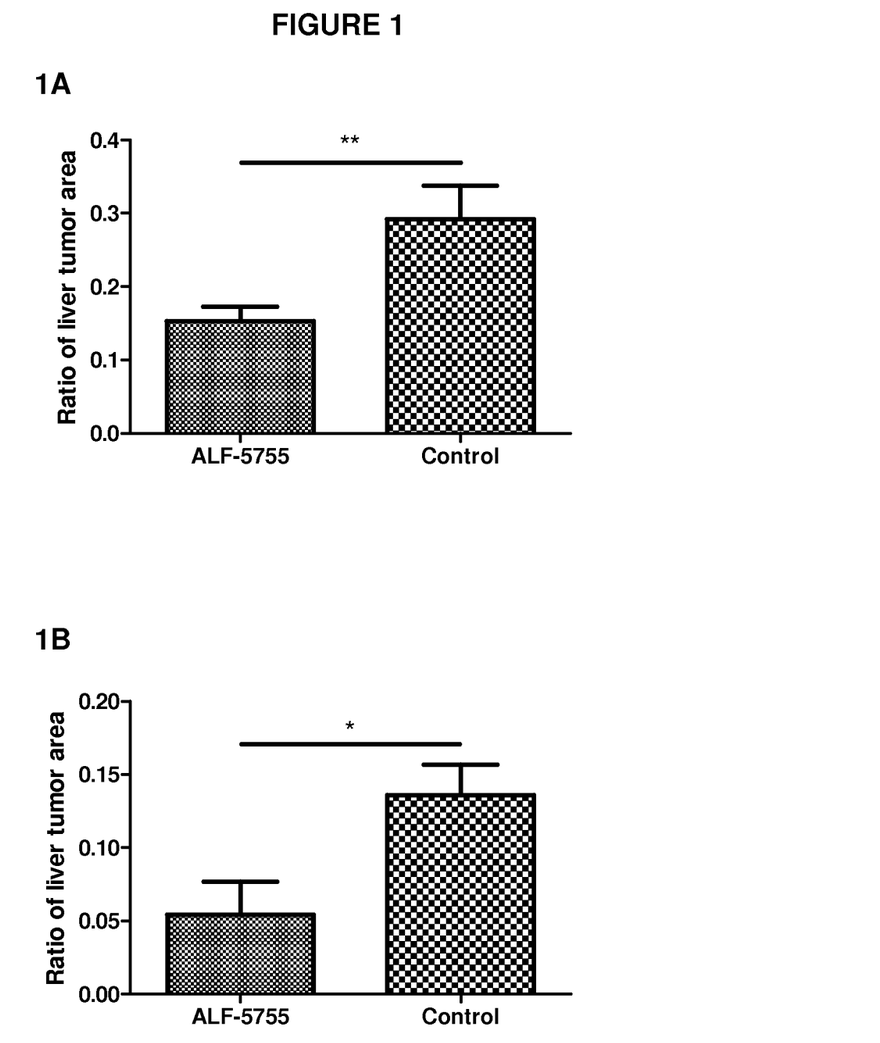
FIG. 1: In vivo effect of HIP/PAP protein on hepatic tumor area after partial hepatectomy (PH).

As shown in FIG. 1A, ALF-5755 lowered hepatic tumor progression after 70% partial hepatectomy (PH) when compared to controls animals that received the vehicle. Among 3 independent experiments, a total of 30 rats received 0.5 mg/kg ALF-5755 in a single injection, and 26 animals received the equivalent volume of buffer. In each experiment, a comparable limitation of tumor progression was observed after ALF-5755 treatment when compared to the control group. In control animals, the tumor liver area represented 29% of the total liver area. This ratio was significantly decreased by about 50% (ratio of 0.29 in controls and of 0.15 in ALF-5755 groups) in ALF-5755 treated animals (p=0.0026, **, one-tailed Mann Whitney test). As shown in FIG. 1B, after 30% partial hepatectomy, ALF-5755 lowered hepatic tumor progression when compared to controls animals that received no injection. In one experiment, a total of 7 rats received 0.5 mg/kg ALF-5755 in a single injection, and 6 control animals were not injected. In control animals, the tumor liver area represented 14% of the total liver area. This ratio was significantly decreased by about 60% (ratio of 0.14 in controls and of 0.05 in ALF-5755 groups) in ALF-5755 treated animals (p=0.022, *, two-tailed Mann-Whitney test).

Example 2

In Vivo Effect of a HIP/PAP Protein on Primary Mammary Cancer

Figure 2:
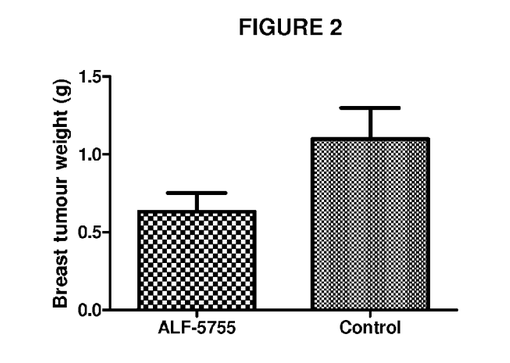
FIG. 2: In vivo effect on primary mammary tumor growth of a HIP/PAP protein infusion.

As shown in FIG. 2, ALF-5755 decrease mammary tumor growth. In a preliminary experiment (exp 1) where mice were injected with 1 million PyMT cells and treated with ALF-5755 (infusion of 43.2 µg per day for 28 days, from the day of implantation) and with doxorubicin (1 weekly intra-tumor injection of 1 mg for 4 weeks from the time when the tumor was detectable; e.g.: day 15 post-implantation in both treated and control groups), ALF tended to decrease tumor growth when associated to doxorubicin as measure by tumor weight at day 45 after implantation. Indeed, tumor weight in control mice was of 1.1±0.2 g (n=2; one animal died during the experiment) and of 0.63±0.12 in the treated group (n=3; no death observed) with a p value close to significance (P=0.059, one-tailed Mann Whitney test).

ALF-5755 treatment protected cancerous mice from death during the time of the experiment. In a preliminary experiment (exp 2) where mice were injected with 1 million PyMT cells and treated with ALF-5755 (infusion of 43.2 µg per day for 28 days, from the day of tumor detection) and +/−doxorubicin (1 weekly intra-tumor injection of 1 mg/kg for 4 weeks from the time when the tumor was detectable; e.g.: day 15 post-implantation in both treated and control groups), In the group that did not received doxorubicin, 3 animals out of 7 that received the placebo died during the course of the experiment; no death was observed in the ALF-5755 treated group. The exact same result was observed in the doxorubicin treated animals. In total 6 placebo treated animals out of 14 died during the experiment when none of the ALF-5755 treated died (n=14) with a P value of 0.008 (**, Fischer exact test). In this experiment analysis of tumor weight could not be performed due to the lack of half of the placebo-treated animals that died possibly from their cancer and for which no post-mortem resection could be performed before cadaveric rigidity.

Example 3

In Vitro Effect of a HIP/PAP Protein on a Pancreatic Cancer Cell Line (PANC1)

Figure 3:
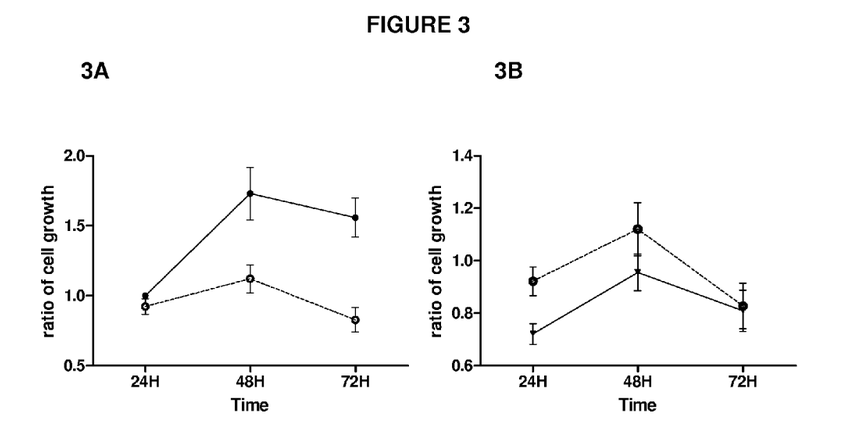
FIG. 3: In vitro effect of HIP/PAP protein on pancreatic cell line (PANC1).

The results for doxorubicin at 2.5 µM on cell density at 24, 48, and 72 hours post-plating are presented in FIG. 3A, as mean of ratio ±SEM. As expected, at this concentration, doxorubicin induced a statistically significant reduction of the cell growth of about 50%. This reduction was effective at 48 hours post-plating and was maintained 72 hours after plating. Two-way ANOVA showed a statistically significant difference between the two paradigms ($F_{(68,1)}=12.66$, $P=0.0011$) reflecting the strong inhibitory effect of doxorubicin, an interaction ($F_{(68,2)}=68\ 2)=10.76$, $P<0.0001$), and a time effect ($F_{(68,2)}=19.26$, $P<0.0001$) indicating a global variation in cell density over time between the cells treated or not with doxorubicin. Post-hoc Bonferonni tests showed that from 48 hours onward, doxorubicin induced a statistically significant decrease in cells growth with P values below 0.001 for 48 hours in the Standard condition and below 0.0001 at 72 hours.

The results for ALF-5755 effect in combination to doxorubicin on cell density at 24, 48, and 72 hours post-plating are presented in FIG. 3B as mean of ratio ±SEM. Results were compared to standard culture condition+doxorubicin). A synergistic effect (additional decrease up to 22% at the time of 24 hours post-plating) was observed for ALF5755 in combination to doxorubicin.

Example 4

In Vitro Effect of a HIP/PAP Protein on a Mammary Cancer Cell Line (MCF7)

Figure 4:
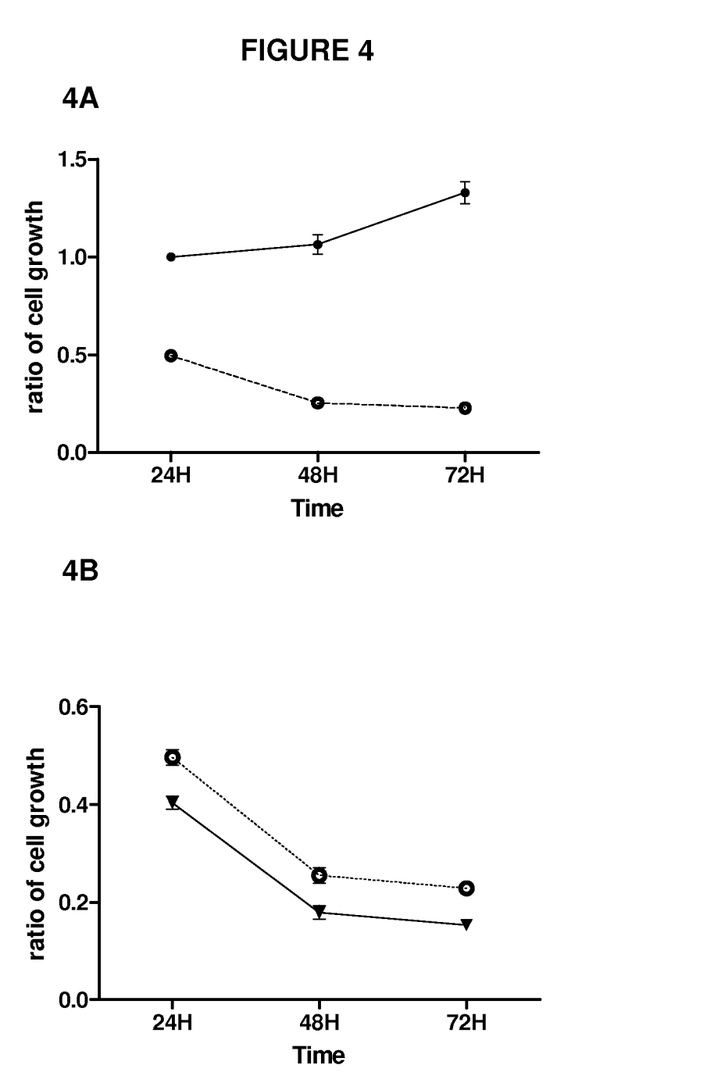
FIG. 4: In vitro effect of HIP/PAP protein on a mammary cancer cell line (MCF7).

As shown in FIG. 4 (A, B) doxorubicin at the concentration of 75 µM was capable of inducing a statistically significant reduction of the growth of MCF7 cancerous cells of about 50% at 24 hours post-plating. This reduction was effective at 24 hours post-plating and was maintained 72 hours after plating. The results for doxorubicin at 75 µM on cell density at 24, 48, and 72 hours post-plating are presented in FIG. 4A as mean of ratio ±SEM. Two-way ANOVA showed a statistically significant difference between the two paradigms ($F_{(68,1)}=1597$, $P<0.0001$) reflecting the strong inhibitory effect of doxorubicin, an interaction ($F_{(68,2)}=35.85$, $P<0.0001$), and a time effect ($F_{(68,2)}=6.21$, $P=0.0033$) indicating a global variation in cell density over time between the cells treated or not with doxorubicin. Post-hoc Bonferonni tests showed that from 24 hours onward, doxorubicin induced a statistically significant decrease in cells growth with P values below 0.0001.

The results for ALF-5755 effect in combination to doxorubicin, on cell density at 24, 48, and 72 hours post-plating are presented in FIG. 4B as mean of ratio ±SEM. Adjunction of ALF-5755 at any of the tested concentrations did not compromise the doxorubicin effect. Furthermore, a synergetic effect of ALF-5755 is observed that increased the doxorubicin effect, with a maximum additional reduction in cell density of 33% at 72 hours. Results were compared to standard culture condition+doxorubicin (standard). Two-way ANOVA showed a statistically significant difference between the two paradigms ($F_{(68,1)}=53.95$, $P<0.0001$) indicating an additional effect of ALF-5755 to that of doxorubicin, no interaction ($F_{(68,2)}=0.29$, $P=0.75$), and a time effect ($F_{(68,2)}=251.6$, $P<0.0001$) indicating a global variation in cell density over time. Post-hoc Bonferonni tests showed that statistical significance was reached at all time with P values below 0.0001.

The invention claimed is:

1. A method for inhibiting tumor or cancer cell growth and/or inhibiting the spread of the cancer, and/or decreasing the tumor size or weight, and/or reducing the number of cancer cells in the body and/or improving or relieving the symptoms of the disease caused by the cancer, comprising the administration of a HIP/PAP protein or derivative thereof to a patient in need thereof, wherein the HIP/PAP derivative is a biologically active derivative comprising an amino acid sequence having at least 90% amino acid identity with a polypeptide of a sequence selected from the group consisting of the polypeptide of SEQ ID NOs. 1, 2, 3, and 4.

2. The method according to claim 1, wherein the cancer is a primary or metastatic breast cancer.

3. The method according to claim 1 wherein said HIP/PAP protein or derivative thereof is administered before, during or after a partial or a total resection of the tumor in the patient in need thereof.

4. The method according to claim 1, wherein the cancer is selected from the group consisting of: lung cancer, cancer of the peritoneum, hepatocellular cancer, gastric cancer, stomach cancer, gastrointestinal cancer, pancreatic cancer, glioblastoma, cervical cancer, ovarian cancer, liver cancer, bladder cancer, cancer of the urinary tract, breast cancer, colon cancer, rectal cancer, colorectal cancer, small intestine cancer, endometrial carcinoma, uterine carcinoma, salivary gland carcinoma, kidney cancer, renal cancer, prostate cancer, vulval cancer, thyroid cancer, hepatic carcinoma, anal carcinoma, penile carcinoma, brain cancer, head and neck cancer.

5. The method according to claim 4, wherein said lung cancer is selected from the group consisting of small-cell lung cancer, non-small cell lung cancer, adenocarcinoma of the lung, and squamous carcinoma of the lung.

6. The method according to claim 1, wherein the cancer is a primary or metastatic digestive cancer.

7. The method according to claim 6, wherein the primary or metastatic cancer is selected from the group consisting of: hepatocellular cancer, liver cancer, gastric cancer, stomach cancer, gastrointestinal cancer, pancreatic cancer, and colorectal cancer.

8. The method according to claim 1, wherein said HIP/PAP or derivative thereof is administered in combination with at least a second active agent for treating or managing cancer and/or any conventional method of treating cancer.

9. The method according to claim 8, wherein the conventional method of treating cancer used in combination is surgery, immunotherapy, biological therapy, or radiation therapy.

10. The method according to claim 8, wherein the at least second active agent for treating cancer used in combination is a cytotoxic agent.

11. The method according to claim 10, wherein the cytotoxic agent used in combination is selected from the group consisting of antimetabolites, antitumor antibiotics, nonsteroidal aromatase inhibitors, immunotherapeutic agents, coordination metal complexes, mitotic inhibitors, topoisomerase inhibitors, hormone therapy agents, alkylating agents, alkaloids, calcium levofolinate, tyrosine kinase inhibitors, monoclonal antibodies, matrix metalloprotease inhibitors, and farnesyl transferase inhibitors.

12. The method according to claim 10, wherein the at least second active agent for treating cancer used in combination is selected from the group consisting of 5-fluorouracile, raltitrexed, epirubicin, hepatinib, methotrexate, doxorubicine, monoclonal antibodies, avastin, oxaliplatin, cisplatin, gemcitabine, docetaxel, lapatinib, oxaliplatin, and daunorubicin.

13. The method according to claim 12, wherein said monoclonal antibody is cetuximab or trastuzamab.

* * * * *